US010350424B2

(12) United States Patent
Doguet

(10) Patent No.: US 10,350,424 B2
(45) Date of Patent: Jul. 16, 2019

(54) PHOTOVOLTAIC ELECTRICAL STIMULATION DEVICE

(71) Applicant: SYNERGIA MEDICAL, Mont-Saint-Guibert (BE)

(72) Inventor: Pascal Doguet, Mont-Saint-Guibert (BE)

(73) Assignee: SYNERGIA MEDICAL, Mont-Saint-Guibert (BE)

(*) Notice: Subject to any disclaimer, the term of this patent is extended or adjusted under 35 U.S.C. 154(b) by 0 days.

(21) Appl. No.: 15/541,063

(22) PCT Filed: Feb. 20, 2015

(86) PCT No.: PCT/EP2015/053585
§ 371 (c)(1),
(2) Date: Jun. 30, 2017

(87) PCT Pub. No.: WO2016/131492
PCT Pub. Date: Aug. 25, 2016

(65) Prior Publication Data
US 2017/0368358 A1 Dec. 28, 2017

(51) Int. Cl.
*A61N 1/04* (2006.01)
*A61N 1/378* (2006.01)
(Continued)

(52) U.S. Cl.
CPC ....... *A61N 1/3787* (2013.01); *A61N 1/36014* (2013.01); *A61N 1/36125* (2013.01);
(Continued)

(58) Field of Classification Search
CPC .............. A61N 1/3787; A61N 1/36014; A61N 1/36125; A61N 1/3752; A61N 1/362; A61N 1/063
See application file for complete search history.

(56) References Cited

U.S. PATENT DOCUMENTS 8,744,568 B2 6/2014 Weber
2002/0116033 A1 8/2002 Greatbatch et al.
(Continued)

FOREIGN PATENT DOCUMENTS

WO 02065895 A2 8/2002
WO 03086538 A1 10/2003
(Continued)

OTHER PUBLICATIONS

International Search Report dated Oct. 20, 2015 for International Application No. PCT/EP2015/053585 filed Feb. 20, 2015.

*Primary Examiner* — Paula J Stice
(74) *Attorney, Agent, or Firm* — Avery N. Goldstein; Blue Filament Law PLLC

(57) ABSTRACT

The present invention concerns an optoelectronic stimulating device for use in a medical treatment involving delivering an electrical current to an electrically excitable tissue ($Z_{bio}$) by means of two electrodes (3n, 3p) electrically coupled to said tissue, said optoelectronic stimulating device comprising: (a) a source (4) of electrical impulses, which is electrically connected to (b) a source of light emission (2), in optical communication with (c) a photovoltaic cell (1) electrically connected to two electrodes (3n, 3p) for establishing two electrical contacts with said tissue and thus forming an electrical stimulating circuit fed by the photovoltaic cell (1) which is energized by the radiation of the source of light emission (2).

16 Claims, 6 Drawing Sheets

(51) Int. Cl.
*A61N 1/375* (2006.01)
*A61N 1/36* (2006.01)
A61N 1/37 (2006.01)
A61B 5/0484 (2006.01)
A61B 5/0488 (2006.01)
A61N 1/05 (2006.01)
A61N 1/362 (2006.01)

(52) U.S. Cl.
CPC .......... *A61N 1/3752* (2013.01); *A61B 5/0484* (2013.01); *A61B 5/0488* (2013.01); *A61N 1/0452* (2013.01); *A61N 1/0456* (2013.01); *A61N 1/0534* (2013.01); *A61N 1/0541* (2013.01); *A61N 1/0551* (2013.01); *A61N 1/362* (2013.01); *A61N 1/3611* (2013.01); *A61N 1/36021* (2013.01); *A61N 1/36038* (2017.08); *A61N 1/36062* (2017.08); *A61N 1/36064* (2013.01); *A61N 1/36067* (2013.01); *A61N 1/36071* (2013.01); *A61N 1/36085* (2013.01); *A61N 1/36096* (2013.01); *A61N 1/36114* (2013.01); *A61N 1/3706* (2013.01)

(56) References Cited

U.S. PATENT DOCUMENTS

| | | |
|---|---|---|
| 2009/0326597 A1 | 12/2009 | Zommer |
| 2010/0217351 A1 | 8/2010 | Choe et al. |
| 2012/0035725 A1 | 2/2012 | Gefen et al. |

FOREIGN PATENT DOCUMENTS

| | | |
|---|---|---|
| WO | 2010148324 A1 | 12/2010 |
| WO | 2014136022 A1 | 9/2014 |

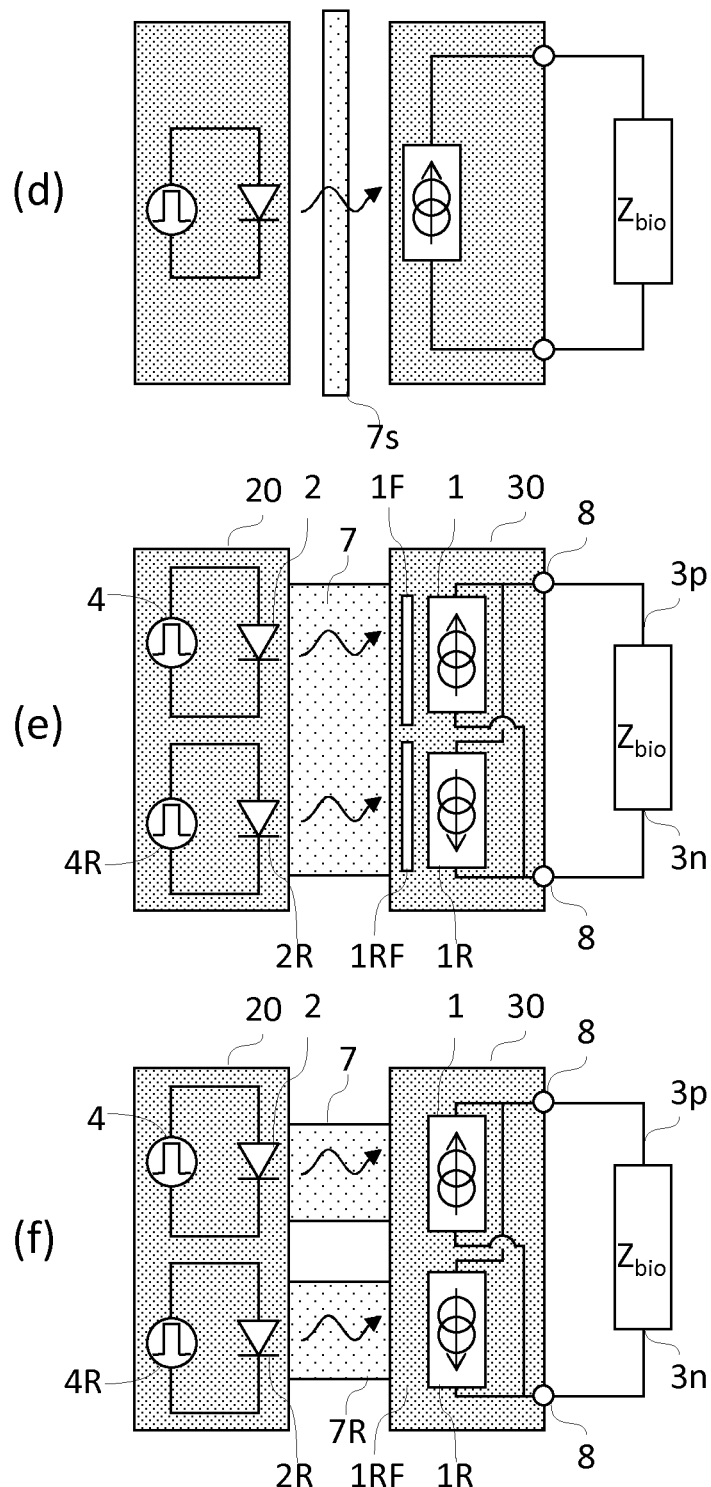
FIG.3 (contd)

PHOTOVOLTAIC ELECTRICAL STIMULATION DEVICE

TECHNICAL FIELD

The present invention concerns an electrical stimulating device for use in a medical treatment involving delivering pulses of electrical current to an electrically excitable tissue, such as a nerve or a muscle, by means of two electrodes electrically coupled to said tissue. In particular, it concerns such device using a light activated photovoltaic cell to generate the current delivered to said tissue.

BACKGROUND OF THE INVENTION

Delivering electrical pulses to a tissue such as a nerve or a muscle has been known in the art for diagnosing or treating a number of disorders such as Parkinson's disease, epilepsy, chronic pain, motor disorders, and many other applications. In its simplest form, a device for delivering such electrical pulses comprises an electrical pulse generator, stimulating electrodes and wires electrically coupling the electrodes to the electrical pulse generator. Depending on the applications, the electrodes can be applied on the skin and the electrical current transmitted transcutaneously to the tissue to be treated. For some applications, however, the electrodes must be applied directly onto the tissue to be treated, requiring the use of an implantable device. It is clear, in the latter case, that miniaturization of the implant is of paramount importance.

Depending on the tissue to be treated, the type of electrodes used, and the distance between electrodes, the voltage required between implanted electrodes is generally of the order of 15V±5V. Such voltage requires an electrical pulse generator of such dimensions that electric stimulating implants are generally formed of two separate components: on the one hand, the electrodes which are implanted directly onto the tissue to be treated and, on the other hand, the electrical pulse generator, of larger dimensions, which can be implanted at various locations in the body depending upon the application but most often in the subclavian region, the lower abdominal area or gluteal region. The wires connecting the pulses generator to the electrodes are generally coiled to provide flexibility, to permit the distance from the electrical pulse generator and the electrodes to be varied and to enhance mechanical stability with a higher compliance with respect to body movements. Because of the use of electric wires, in particular when coiled, such implants are incompatible with magnetic resonance imaging (MRI) apparatuses and also with simple metal detecting portals as used in airports, banks, and the like.

As shown in FIG. 1(b), digital-analog converters (DAC) are usually used to deliver the required current and voltage to the stimulating circuit, but few are satisfactorily accurate at voltages greater than 5V or even than 10 V, while still providing sufficient current resolution and with a power consumption compatible with an implantable device.

The Compound Action Potential (CAP) is the algebraic sum of all individual fibre action potentials of a tissue stimulated by electrodes. Recording the CAP is important because it reveals the reactivity of the tissue to the stimuli, the threshold voltage, the latency of the beginning of the CAP, distribution of fibres types making up the stimulated tissue, etc. The recording of the CAP response near the stimulation point is quite challenging because of the small amplitude of the nerve CAP (typically a few tens of µV while the stimulus is in the range of 5 to 15 volt, resulting in a large contamination of the recording input by the stimulus artefact that severely obscures the genuine CAP signal.

The electrical pulse generator in electrical stimulating implants is generally powered by a battery, either primary (non-rechargeable) or rechargeable. A rechargeable battery must be recharged at regular intervals, while the number of recharge cycles reduces the battery life and capacity, which may range from one day to several months depending on the applications and type and size of the battery. As discussed above, the battery is generally implanted remotely from the tissue to be stimulated, in places such as in the sub clavicular space, the abdominal area or the gluteal region. The battery can be recharged transcutaneously by means known in the art. For example, an implantable medical device may include a solar cell configured to provide energy to recharge a power source such as a battery. The solar cell may be implanted in the body of a host such that a surface of the solar cell is provided under a layer of translucent skin, which allows the solar cell to receive light from outside the body. Examples of such systems are disclosed in US20090326597, WO2014136022, or US20120035725.

U.S. Pat. No. 8,744,568 proposes a medical device comprising an implantable electroactive polymer which is electrically stimulated by a photovoltaic cell as a source of electrical power. This device can be used in particular for releasing a therapeutic agent in situ. This device is, however, not used for electrically stimulating a tissue.

There remains a need in the art for tissue electrical stimulating devices which are safe, reliable, have a long autonomy. It should also be compatible with MRI, allow CAP recording near the stimulated point and, for implants, being of small size. The present invention proposes such device. These and other advantages of the present invention are presented in the next sections.

SUMMARY OF THE INVENTION

The present invention is defined in the appended independent claims. Preferred embodiments are defined in the dependent claims. In particular, the present invention concerns an optoelectronic stimulating device for use in a medical treatment involving delivering an electrical current to an electrically excitable tissue by means of two electrodes electrically coupled to said tissue, said optoelectronic stimulating device comprising:

(a) a source of electrical impulses, which is electrically connected to
(b) a source of light emission, in optical communication with
(c) a photovoltaic cell electrically connected to two electrodes for establishing two electrical contacts with said tissue and thus forming an electrical stimulating circuit fed by the photovoltaic cell (which is energized by the radiation of the source of light emission.

In a preferred embodiment, the source of electrical impulses is suitable for making the source of light emission to emit calibrated pulses of light of a duration comprised between 1 µs and 10 ms, preferably between 10 µs and 1 ms. The photovoltaic cell may be selected such that when energized by the source of light emission, it delivers charges comprised between 0.01 and 50 µC, preferably between 0.1 and 10 µC, preferably at a higher voltage than the voltage available from the source of electrical impulses.

In practice, it is preferred that the optoelectronic stimulating device further comprises a housing containing the source of electrical impulses and being physically separate from the electrodes. The stimulating device may thus present one of the following configurations:

(a) The housing also contains the source of light emission, the photovoltaic cell and comprises electrical connectors suitable for electrically connecting the photovoltaic cell to the two electrodes to form the electrical stimulating circuit; or (b) The housing also contains the source of light emission and is connected to a fibre optic for transmitting the light emitted by the source of light emission to the photovoltaic cell enclosed in a casing located separate from the housing and, adjacent to the electrodes; or (c) The casing encloses the photovoltaic cell and the source of light emission which is in electrical contact with the source of electrical impulses contained in the housing, In order to prevent damaging side effects, it is preferred that the optoelectronic stimulating device further comprises a, a recovering source of light emission in optical communication with a recovery photovoltaic cell electrically connected to the two electrodes for establishing two electrical contacts with said tissue and thus forming an electrical charge recovering circuit in parallel with the electrical stimulating circuit and fed by the recovery photovoltaic cell, such that when the recovery photovoltaic cell is energized by the recovery source of light emission, a current flows through the tissue in a direction opposite to the current flowing in the electrical stimulating circuit, so as to remove any electrochemical charge accumulated at the electrode-tissue interface.

For safety reasons and to prevent transmission of a direct current (DC) to the stimulating circuit, it is preferred that the optoelectronic stimulating device further comprising a DC-blocking circuit comprises a safety capacitance (5) placed in series with the source of light emission.

An optoelectronic stimulating device according to the present invention may comprise a wireless control system indicative of the current actually delivered to a tissue during a stimulation sequence. In one embodiment, said control system may comprise a source of control light emission located in series with the electrodes and the photovoltaic cell, said source of control light emission emitting a light when electrically activated, the device further comprising a light emission sensor in optical communication with the source of control light emission and coupled to a processor programmed to record the pulses emitted by the source of control light emission, said processor being preferably part of the source of electrical impulses.

In an alternative embodiment, said control system may comprise a control circuit, comprising:

(a) a control photovoltaic cell (1C) in optical communication with the same source (2) of light emission as the photovoltaic cell (1) of the stimulating circuit, (b) a source of control light emission (13) emitting a light when electrically activated by the control photovoltaic cell (1R), the device further comprising (c) a light emission sensor (9) in optical communication with the source (13) of control light emission and coupled to a processor programmed to record the pulses emitted by the source of control light emission, said processor being preferably part of the source of electrical impulses.

The optoelectronic stimulating device may be in the form of an implant, designed such that at least the electrodes can be implanted near the tissue to be electrically stimulated. A housing containing at least the source of electrical impulses can be implanted at a location remote from the tissue to be electrically stimulated. In a preferred embodiment, a casing containing at least the photovoltaic cell can be implanted adjacent to the electrodes and to the tissue to be electrically stimulated.

The electrically excitable tissue to be fed with electrical current is preferably selected from (a) neural tissues and (b) muscular tissues. An optoelectronic stimulating device according to the present invention can be used for diagnostic and therapeutic application both on neural and muscular tissues in a number of medical applications. Besides implantable devices, an optoelectronic stimulating device according to the present invention may stimulate a tissue transcutaneously by applying the electrodes onto the skin of a patient, rather than implanting them. Extracorporeal devices can similarly be used in a number of diagnostic and therapeutic applications.

BRIEF DESCRIPTION OF THE FIGURES

For a fuller understanding of the nature of the present invention, reference is made to the following detailed description taken in conjunction with the accompanying drawings in which.

DETAILED DESCRIPTION OF THE INVENTION

Figure 1:
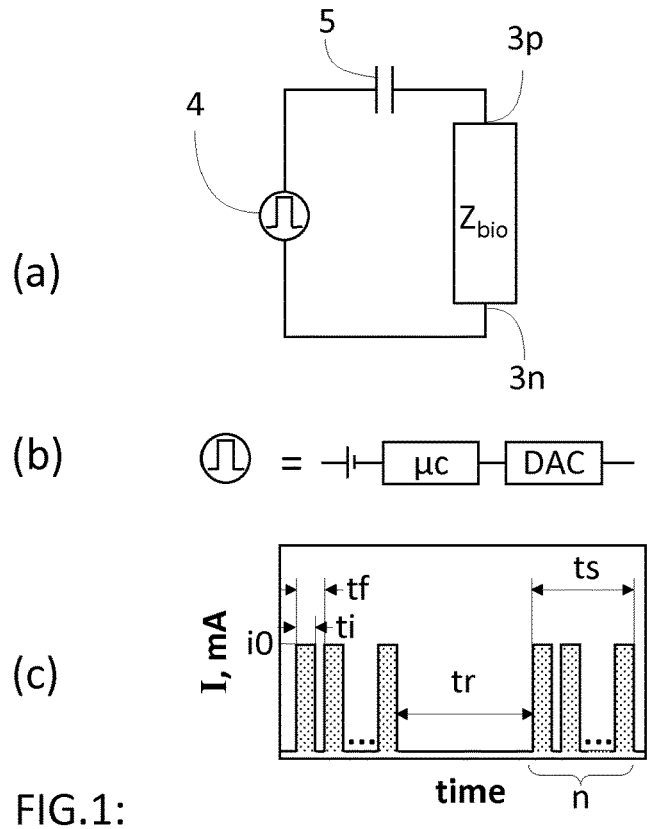
FIG. 1: shows (a) an example of electrical stimulating device of the prior art, (b) an example of source of electrical impulses, and (c) and example of electrical pulses sequence.

As illustrated in FIG. 1(a), a traditional electric pulse stimulating device comprises a source (4) of electrical impulses coupled to electrodes (3n, 3p) which are applied onto the skin in the region of the tissue to be stimulated in case of extracorporeal electrodes, or directly onto the tissue to be treated, in case of implanted devices. The tissue to be stimulated is represented as $Z_{bio}$ in the Figures. A capacitance is usually added in the circuit for safety reasons, to prevent a DC current to be accidentally delivered to the tissue.

The source (4) of electrical impulses must be able to deliver very accurately calibrated pulses of electrical current of intensity comprised between 0.01 and 100 mA and higher, and of duration comprised between 1 μs and 10 ms, preferably between 10 μs to 1 ms. An example of source (4) of electrical current is represented in FIG. 1(b), comprising a generator, such as a battery, a microcontroller (μc) programmed to deliver calibrated pulses of required shape, intensity (i0), duration (ti) and at the required frequency (1/tf), and a digital-to-analogic converter (DAC) to convert the digital signal of the μc into analogic current sent to the electrodes. The resolution is generally required to be of at least 8 bits to ensure the required selectivity and fine tuning.

An electrical stimulating device according to the present invention, as well as according to the prior art, must be able to deliver charges of the order of 0.01 to 50 μC, preferably 0.1 to 10 μC to the tissue to be treated. For implanted electrodes, the resistance of the tissue, $Z_{bio}$, is of the order of the 3-5 kΩ. With a current of the order of mA, such as 0.1-3 mA, the voltage required between electrodes is of the order of 10 V. For surface stimulation devices using extracorporeal (or transcutaneous) electrodes, the resistance of the tissue, $Z_{bio}$, is substantially higher, with typical values of the order of 100 kΩ, and for 100 μs long current pulses of the order of not more than 100 mA, a voltage of the order of up to 300 V may be required between the electrodes. Depending on the application, the duration of the electrical impulses may range from 1 μs to 10 ms, preferably from 10 μs to 1 ms.

As discussed in the introduction, the delivery of electrical current through relatively long wires, which are generally coiled, is disadvantageous because they are incompatible with MRI and magnetic metal detecting portals. Furthermore, the current requirements of electrical stimulating devices are such that they require large capacity batteries and/or frequent charging of the battery, which is a long and tedious operation for the patient if repeated frequently.

As illustrated in FIG. 2(a), an electrical stimulating device according to the present invention differs from the prior art devices in the way the electrical pulses delivered by the source (4) of electrical impulses arrive at the electrodes. The source (4) of electrical impulses can be of the type represented in FIG. 1(b). The gist of the present invention lies in that the current is not delivered directly from the pulses generator (4) to the electrodes (3n, 3p) contrary to the devices of the prior art, but to a source of light emission (2). The source of light emission (2) is advantageously a light emitting diode (LED), or a laser LED. The term "light" is used herein in a broad sense, not limited to visible light. A source of light emission (2) suitable for the present invention should be able to emit a light having a wavelength comprised between 300 and 2000 nm, preferably between 400 and 1800 nm, more preferably between 700 and 1550 nm. The light emitted is preferably monochromatic.

The energy of the light pulses emitted by the source of light emission (2) when current, I4, is delivered by the source (4) of electrical impulses is transformed into electrical current by means of a photovoltaic (PV) cell (1) positioned in optical communication with the source (2) of light emission and delivering a current, I1. A photovoltaic cell (2) comprises an absorption material (e.g., a semiconductor doped or not) absorbing and converting light into electric current, I12. One of the key properties of a photovoltaic cell is the optical power conversion (OPC), which measures a material's ability to convert light into an electric current. The optical power conversion of a given photovoltaic cell depends of course on the wavelength of the absorbed light. The type of photovoltaic cell must therefore always be selected in combination with the source of light emission most appropriate for use with such photovoltaic cell. Higher optical power conversions are achieved with is monochromatic light and OPC values of up to 50% have been reported in the literature. The most commonly used photovoltaic cells comprise amorphous, mono-, or poly-crystalline silicon PV cells, cadmium telluride PV cells (CdTe), copper indium gallium selenide PV cells (CI(G)S), gallium arsenide germanium PV cells (GaAs), and the like.

As illustrated in FIG. 2(b), the absorption material (12) of a photovoltaic cell is generally modelled as a PV circuit (10) comprising a source of current (12) in parallel with a diode (11), and with resistances in series and parallel. The voltage output for such a PV circuit depends upon the load applied thereto and on the properties of the diode. In order to broaden the voltage output range of a photovoltaic cell (1), several such PV circuits (10) can be disposed in series, as indicated by "Nx" in FIG. 3(b).

Each photovoltaic cell is characterized by a current vs voltage curve available from the supplier, with a linear, substantially constant intensity delivered independently of the voltage, which is limited by a maximum power threshold defining the voltages above which the current drops suddenly. It is clear that the photovoltaic cells (1), used alone or in combination with other photovoltaic cells (cf. FIG. 6), must be selected as a function of the desired voltage required at the electrodes, such that for the desired current, said voltage is well within the linear portion of the current vs voltage curve (i.e., well below the power threshold). A person skilled in the art knows how to ensure this requirement is satisfied.

The current is delivered to the electrodes (3n, 3p) directly from the photovoltaic cell (1) and not, like in the prior art, by the source (4) of electrical impulses. This has many advantages. For example, when a voltage of the order of 10 V is required between implanted electrodes (3n, 3p), the source (2) of light emission requires much lower voltage, of the order of 0.5 to 4.5 V, preferably of 0.8 to 3 V, with obvious advantages in terms of reduced size and prolonged autonomy of the source (4) of electrical impulses. For example, contrary to a device as illustrated in FIG. 1(a), no DC-DC converter is required in a device of the present invention to boost the available battery voltage up to the required high output voltage.

Furthermore, during a series of electrical pulses current is required by the system only during stimulation. For example, FIG. 1(c) shows an example of stimulation pulse sequence, comprising two stimulation series of duration, ts, each comprising n pulses (here square) of intensity, i0 and duration, ti, repeated at a frequency of 1/tf, and separated by a rest period, tr. By contrast, in a stimulation device of the prior art as represented in FIG. 1(a), part of the current generation circuit and high voltage analog front-end need to be powered at all time or require a long power up time incompatible with the duration between stimulation pulses. It follows that such stimulation device of the prior art would require energy to be delivered by a battery during the whole stimulation period, ts, of a series of n pulses represented in FIG. 1(c) (viz., n×tf), current in a device according to the present invention only requires current during when light pulses are being emitted by the source (2) of light emission, i.e., during a time=(n×ti)<(n×tf). For example, a stimulating sequence representative of treatment of epilepsy, characterized by n=30 pulses of duration, ti=250 μs at a frequency, 1/tf=1 Hz, for a stimulation period, ts=30 s, and rest period, tr=300 s, the ratio, $t_{inv}/t_{PA}$, of the time, $t_{inv}$, the source (2) of light emission must be energized to the time, $t_{PA}$, a circuit according to FIG. 1(a) must be energized is equal to 0.03%. At a frequency, 1/tf=30 Hz, n=900 and the ratio, $t_{inv}/t_{PA}$=ti/tf=0.75%.[1] It follows that during the duration, ts, of a stimulating sequence of n pulses, a stimulating device according to the present invention is energized only a small fraction of the time a stimulating device of the prior art is energized (in the two examples supra, less than 1% of the time (i.e., $t_{in}/t_{P4}<1\%$)), resulting in a considerably lower energy consumption.

$t_{in}/t_{P4}$=n×ti/n×tf=ti/tf: –If 1/tf=1 Hz, $\Rightarrow t_{in}/t_{P4}$=250 μs/1 s=2.5 $10^4$. If 1/tf=30 Hz, $\Rightarrow t_{in}/t_{P4}$=250 μs×30 $s^{-1}$=0.75%

The combined two foregoing effects—lower voltage and shorter energizing time—permit to reduce considerably the size of the source (4) of electrical pulses, and/or to prolong the autonomy of the battery, thus requiring substantially less frequent battery recharging sessions, to the benefit and comfort of the host of an implant. Other applications than epilepsy discussed above require other types of stimulating sequences. The pulses sequence of FIG. 1(c) is particularly simple and a person skilled in the art knows that many different sequences are possible.

The source of electrical impulses (4) of an optoelectronic stimulating device according to the present invention should be suitable for making the source of light emission to emit calibrated pulses of light of a duration comprised between 10 μs and 10 ms. The source (2) of light emission and the photovoltaic cell (1) should be selected such that, during each pulse, charges comprised between 0.01 and 50 μC, preferably between 0.1 and 10 μC are delivered by the photovoltaic cell (1) at the desired voltage, preferably of the order of 5-30 V, preferably of 15 V±7V for implanted devices, and of the order of up to 300 V for extracorporeal devices. It is advantageous if the voltage delivered by the photovoltaic cell (1) is higher than the voltage available from the source of electrical impulses (4), which can be of the order of 0.5 to 4.5 V, preferably of 0.8 to 3 V.

As illustrated in FIG. 3(a), the whole stimulation circuit can be enclosed in a housing (20) with electrical connectors (8) for connecting electric wires ending in the electrodes (3n, 3p). This configuration would be similar to the one conventionally used in prior art implanted electrical stimulators, with the advantage of a lower energy consumption. For extracorporeal electrodes, the use of electric wires presents obvious advantage for safety issues related to any system comprising a current generator electrically coupled to a body, since the electrodes (3n, 3p) are electrically separated and insulated from the source (4) of electrical impulses. For implanted electrodes, on the other hand, the use of electrically conducting wires is incompatible with MRI apparatuses.

An optoelectronic stimulating device according to the present invention is highly advantageous, because all the elements of the stimulating circuit, excluding the battery, are very small and can be integrated in an integrated circuit (IC) enclosed in a casing (30) of very small size, with very limited power consumption and heating. It follows that, when the battery can be contained in the housing (20), the rest of the stimulating circuit can be located adjacent to the electrodes. For example, as illustrated in FIG. 3(b), the source (4) of electrical impulses can be stored in a housing (20); whilst all the other elements, including the source (2) of light emission, and the photovoltaic source can be integrated in the same encapsulation (30).

By moving the source (2) of light emission into the housing (20) containing the source (4) of electrical impulses, an electric wire free system can be obtained as illustrated in FIG. 3(c), wherein light emitted from the housing (20) is transmitted to the encapsulation (30) containing the photovoltaic cell (1) located near or on the electrodes (3n, 3p) by means of a fibre optic (7). This has the advantage of being fully MRI compatible contrary to the devices comprising electrically conductive wires.

In the embodiment illustrated in FIG. 3(d), the source (2) of light emission and the source (4) of electrical impulses are located out of the host's body, whilst the photovoltaic cell (1) is implanted subcutaneously and exposed to the light emitted and transmitted through the skin (7s). This embodiment too is devoid of electrically conductive wire, but suitable only for intermittent treatments since the photovoltaic cell (1) must be exposed to an external source (2) of light emission.

Figure 4:
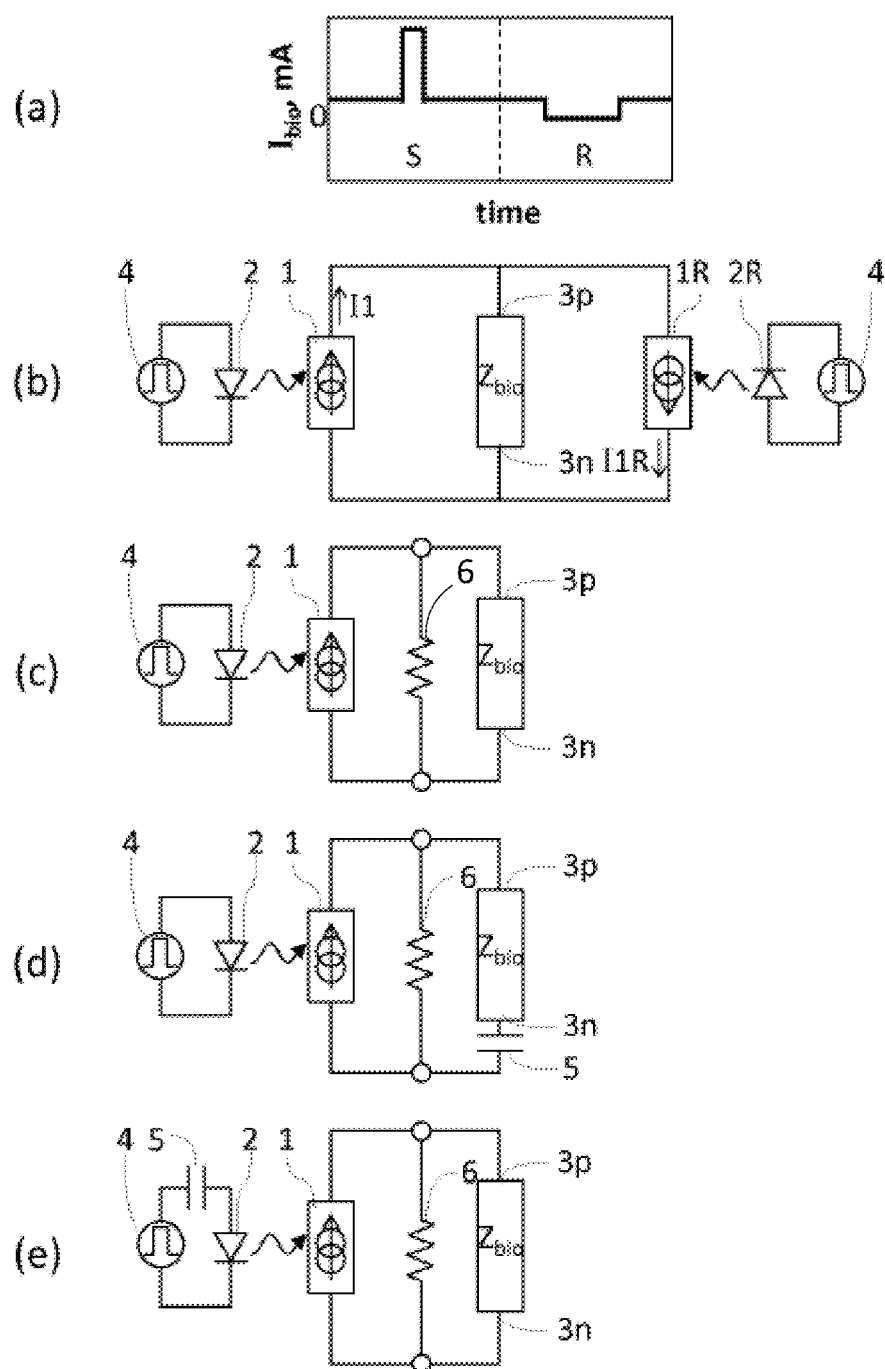
FIG. 4: shows (a) a stimulating impulse followed by a recovery impulse; and the remaining figures (b) to (d) show a stimulating circuit according to the present invention (b) coupled to a recovery circuit, (c) comprising a resistance in parallel, (d) comprising a capacitance in series and a resistance in parallel, and (e) wherein the light emission circuit comprises a capacitance.

The charges delivered to a tissue must be recovered, lest irreversible electrochemical changes would take place. For this reason, it is preferred that the electrical circuit be made bipolar, i.e., that current can circulate in both directions. The stimulation circuit transports charges in a first direction to stimulate the tissue, and an electric charge recovery circuit is formed transporting charges in the opposite direction. This process is illustrated in FIG. 4(a) showing an electrical stimulating pulse (S) followed by a balanced charge recovery pulse (R), which should ideally have the same current× time area as the stimulating pulse. An example of recovery circuit is illustrated in FIG. 4(b). The portion of circuit located on the left hand side of the tissue ($Z_{bio}$) to be treated is the stimulating circuit as discussed above and corresponding to the circuit illustrated in FIG. 2(a). The circuit on the right hand side of the tissue ($Z_{bio}$) is the recovery circuit mounted in parallel with the stimulating circuit, and only differing from the latter in that the direction of the current, I1R, is inverted with respect to the current, I1, of the stimulating circuit. The electrical charge recovery circuit comprises its own source (2R) of light emission and its own photovoltaic cell (1R). The stimulating circuit and recovery circuit are meant to be activated alternatively, not simultaneously.

Another embodiment of a recovery circuit is illustrated in FIG. 3(e), showing the independent source (4, 4R) of electrical impulses, sources (2, 2R) of light emission, and photovoltaic cells (1, 1R) positioned in parallel and in opposite orientations. In this embodiment, the two sources (2, 2R) of light emission are located in a housing (20) optically connected by means of a fibre optic to a casing (30) containing the two photovoltaic cells (1, 1R). In order to prevent the two photovoltaic cells (1, 1R) to be activated simultaneously, filters (1F, 1RF) are positioned between the sources (2, 2R) of light emission and the photovoltaic cells (1, 1R). The sources (2, 2R) of light emission preferably emit in different monochromatic spectra, and the stimulating filter (1F) cuts off the wavelength of the recovery source (2R) of light emission, while the recovery filter (1RF) cuts off the wavelength emitted by the stimulating source (2) of light emission. With this simple system, simultaneous activation of the stimulation and recovery circuits can be avoided while using a single fibre core for light transmission from both sources (2, 2R) of light emission. Another option, not necessarily requiring filters (1F, 1RF) and allowing sources of light emission of the same wavelength to be used, is to use two separate fibre cores (7, 7R), each core serving for transmitting light from one of the two sources (2, 2R) exclusively to the corresponding photovoltaic cell (1, 1R). The two cores can be enclosed within a single fibre cladding (cf. FIG. 3(f)).

Other recovery systems are possible. For example, as illustrated in FIG. 4(c) a recovery resistor is positioned in parallel with the photovoltaic cell (1). In FIG. 4(d) a capacitance (5d) positioned in series with the photovoltaic cell (1) allows the recovery of charges. Of course, the charges recovered by a capacitance need to be discharged at a later stage. The circuit illustrated in FIG. 4(e) comprises a capacitance (5) located in series in the circuit of the source (2) of light emission. This system offers a high level of safety, because if no current reaches the source (2) of light emission, no current can possibly be generated in the stimulating circuit by the photovoltaic cell (1). This is clearly an advantage as a DC discharge in the tissue is virtually impossible.

Figure 5:
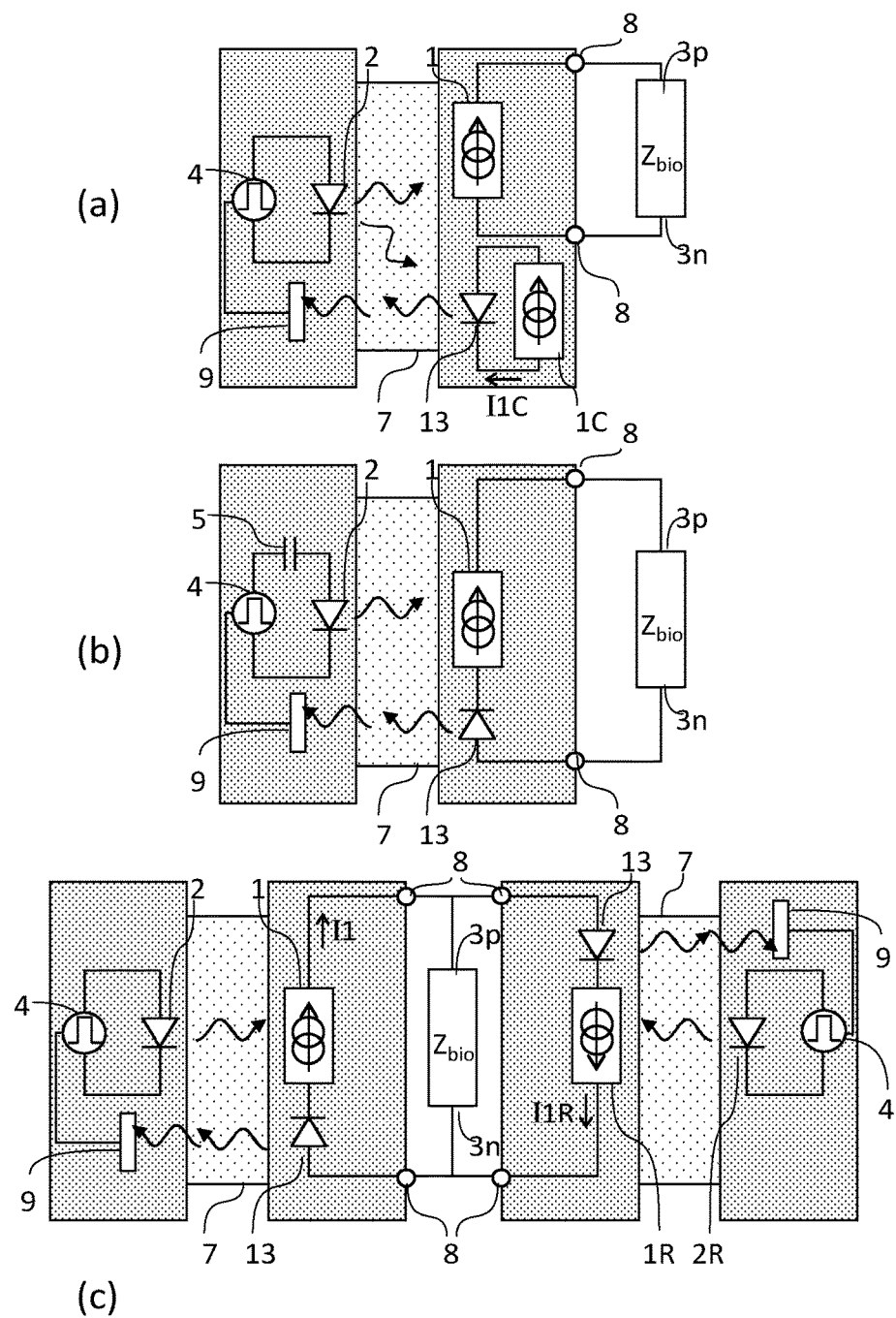
FIG. 5: shows various embodiments to provide a feedback on the pulses transmitted to the stimulated tissue.

Recording of the Compound Action Potential (CAP), i.e., the current actually flowing through the tissue ($Z_{bio}$) is an important feedback for the person in charge of the treatment. Such recording is quite difficult because it requires measuring the signal adjacent to the electrodes with additional wiring extending between a processor and the electrodes. Whilst for a complete CAP measurement such extra wiring is also required with a device of the present invention, the latter allows the stimulating circuit to be electrically isolated from the CAP measurement circuit, facilitating the measurement by eliminating the stimulus artefact. The invention also allows the wireless recording of the current actually transmitted to the stimulated tissue by the photovoltaic cell (1). By ensuring that the signal emitted by the source (4) of electrical impulses was actually delivered to the treated tissue, such feedback systems can detect faults in the optic transmission. Feedback information can also be completed by a full electrode potential measurements, which provides values of the electrodes impedance and confirms the activation of the target tissue required for an evaluation of the physiological parameters. FIG. 5 shows various embodiments allowing feedback measurements of the generated current at the PV cell or at the electrodes.

FIG. 5(*a*) shows an embodiment comprising a control photovoltaic cell (1C) exposed to the same source (2) of light emission as the photovoltaic cell (1) of the stimulating circuit by means of a single fibre optic (7). A light emitting diode is coupled to the control photovoltaic cell (1C) and emits light when the latter is activated by current, I1C. A light emission sensor (9) located at the other end of the fibre optic and coupled to the microcontroller is provided to record all light signals indicative that the source (2) of light emission did reach the photovoltaic cell (1) as well as the control cell (1C).

When the control system of FIG. 5(*a*) is indirect in that the current is not measured directly on the stimulating circuit, the embodiment of FIG. 5(*b*) is a direct control system. A light emitting diode (13) (LED) is positioned in series in the stimulating circuit. Whenever current circulates in the stimulating circuit the LED (13) emits light received by a light emission sensor (9) coupled to the microcontroller. This embodiment gives a direct recording of stimulating current actually delivered to the tissue in an extremely compact form, requiring no extra wiring.

The embodiment of FIG. 5(*c*) is the same as the one discussed with respect to FIG. 5(*b*) with an additional recovery circuit. Both stimulating and recovery circuits are provided with a LED (13) positioned in series in the respective circuits. A light emission sensor (9) is provided for both LED's and coupled to the microcontroller which can then record the CAP of the device both in stimulating and recovering modes.

Figure 6:
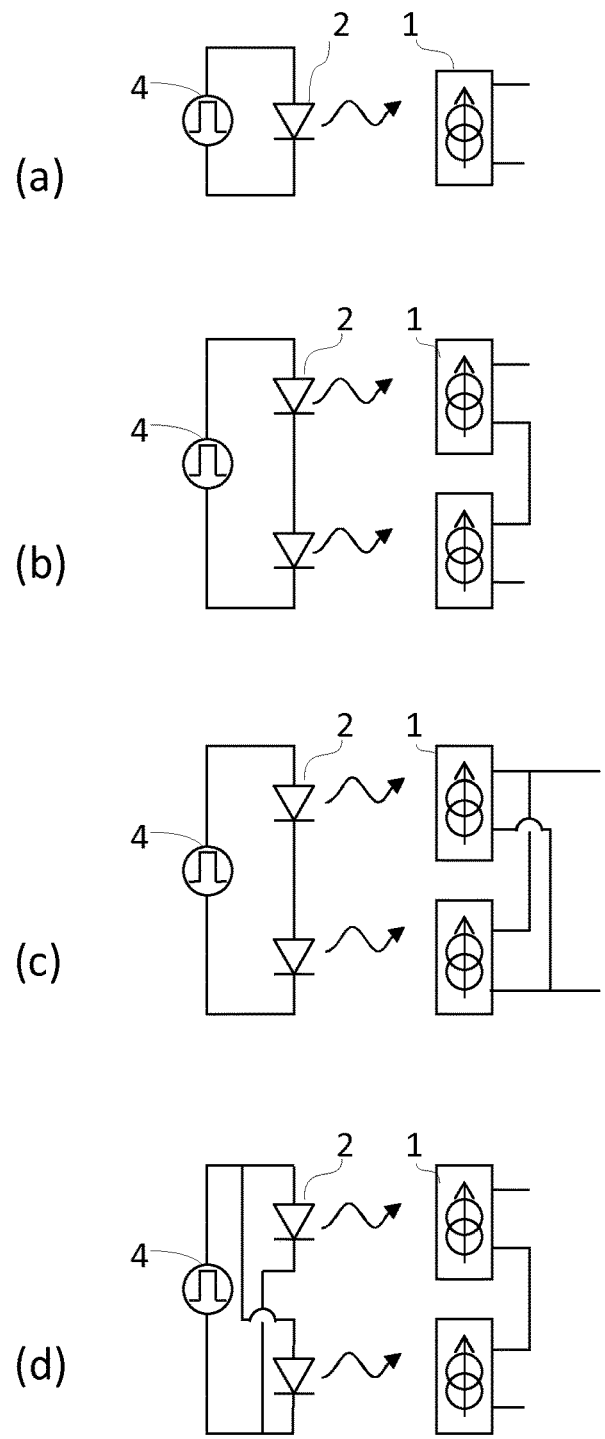
FIG. 6: shows various configurations of the source of light emission and of the source of electrical impulses.

An optoelectronic stimulating device according to the present invention is very advantageous in that it is a high voltage precision current source. Furthermore, it is very versatile, and by assembling a few basic elements, it can be adapted to various requirements, such as the voltage output dynamic at the electrodes. FIG. 6(*a*) shows a basic assembly of a given source (4) of electrical impulses, a source (2) of light emission and a photovoltaic cell (1), corresponding to the device represented in FIG. 2(*a*). As shown in FIG. 6(*b*), the voltage available at the electrodes can be increased by positioning photovoltaic cells (1) in series. This is an important feature because, as discussed earlier, the voltage required at the electrodes varies from values of the order of about 10 V and more for implanted electrodes and up to about 300 V for extracorporeal electrodes. Alternatively, the photovoltaic cells (1) can be positioned in parallel to increase the current intensity as illustrated in FIG. 6(*c*).

The assembly in different configurations of several sources (2) of light emission such as LED's (2) can also be advantageous depending on the voltage of the source (4) of electrical impulses. For example, if the voltage of the source (4) of electrical impulses is relatively low, e.g., about 1.8 V, the LED's (2) could preferably be positioned in series as shown in FIG. 6(*b*)&(c). On the other hand, with a source (4) of electrical impulses delivering a higher voltage, e.g., 3.7 V, it may be advantageous to position the LED's in parallel as shown in FIG. 6(*d*); in order to prevent voltage drops as the current delivery is decreased. The flexibility of the present device by arranging basic components in different configuration is very advantageous and reduces production costs. Other arrangements of several sources (2) of light emission and photovoltaic cells (1) in series, in parallel, or combinations of series and parallel arrangements are possible.

The optoelectronic stimulating device of the present invention is also very advantageous for the following reasons. First, it fulfils the requirements for tissue stimulating devices. In particular, it is capable of delivering to the electrodes (3n, 3p) the required current in the order of 0.01-100 mA, and more particularly of the order of 0.1 and 3 mA. The desired voltages at the electrodes can easily be delivered for both implanted electrodes, with voltages of the order of 10 V and more, and extracorporeal electrodes, with voltages which can go up to 300 V. The device can easily provide at least 8-bit resolution for selectivity and fine tuning. It can be equipped with a very efficient recovery circuit yielding a bipolar system. The optoelectronic stimulating device of the present invention is therefore suitable for use in medical applications. It is, however, advantageous over existing stimulating devices for the following reasons.

Figure 2:
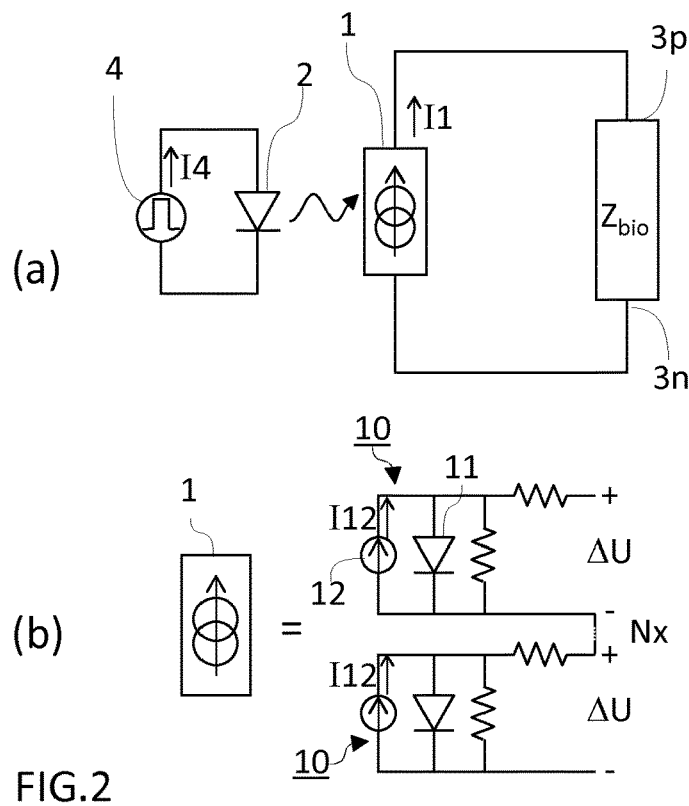
FIG. 2: shows (a) an electrical stimulating device according to the present invention, and (b) an example of photovoltaic cell.

The optoelectronic stimulating device of the present invention is much more compact than existing devices of the type depicted in FIG. 1(*a*). Not only it requires a smaller battery (or the same battery has a longer autonomy) because consuming less power than devices according to FIG. 1(*a*), but the photovoltaic cell (1) and optionally the source (2) of light emission can be compacted to such extent that they can be located adjacent to the electrodes, even for implanted electrodes. This gives the possibility to use fibre optics in place of any electric wiring which is incompatible with MRI apparatuses and magnetic metal detector portals, in particular when the wiring is coiled. With the versatility afforded by various combinations of basic elements, the optoelectronic stimulating device of the present invention can be adapted to most specific medical applications, regardless of the type of tissue to be stimulated and the required voltages and currents required for each application. The voltage of the source (4) of electrical impulses needs not match the required voltage between the electrodes (3n, 3p). Furthermore, it is very safe, a very important feature for medical devices. The leakage (dark current) in such devices is negligible, of the order of less than 100 nA. Besides the safety features known in the art, a capacitance positioned in the light emission circuit practically rules out any delivery of DC current to the electrodes.

Medical Applications

Figure 3:
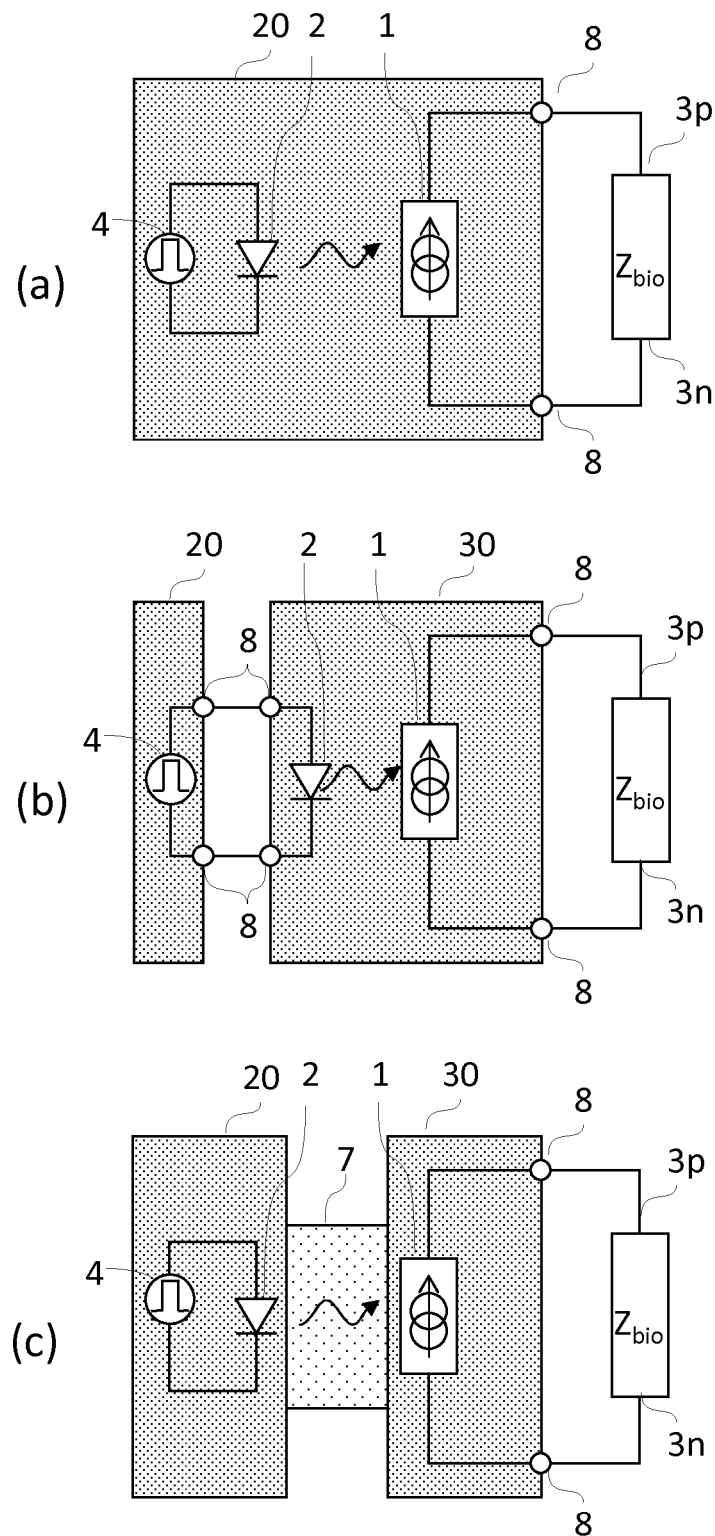
FIG. 3: shows various embodiments of the present invention with the source (4) of electrical impulses, the source (2) of light emission, and the photovoltaic cell (1) disposed in different configurations.

An optoelectronic stimulating device according to the present invention can be used to electrically stimulate electrically excitable tissues ($Z_{bio}$) selected from (a) neural tissues and (b) muscular tissues. The electrodes can be implanted and applied directly on the tissue to be stimulated or, alternatively, they can be applied on the skin, at the region where the tissues to be stimulated are located. In case of implanted electrodes, all embodiments are possible as long as the electrodes are implanted. In particular, the photovoltaic cell (1), the source (2) of light emission, and the source (4) of electrical impulses can be implanted or not. As discussed with reference to FIG. 3, even if all the elements of the device are implanted, they can be implanted at different regions of the host's body. A feature unique to the present invention is that the photovoltaic cell (1) and optionally the source (2) of light emission can be miniaturized to such extent that they can be implanted adjacent to the electrodes and to the tissue to be stimulated, whilst only the source (4) of electrical impulses and optionally the source (2) of light emission is implanted separately, and can be wireless, using fibre optics for transmitting light to the photovoltaic cell (1) as illustrated in FIG. 3(c).

Implantable optoelectronic stimulating devices according to the present invention can advantageously be used to stimulate (a) neural tissues ($Z_{bio}$) in any of the following applications:

(a1) Deep brain stimulation for the treatment of Parkinson's disease, epilepsy, depression, obsessive compulsive disorder, dystonia, essential tremor, pain, or blindness;

(a2) Cortical brain stimulation for the treatment of deafness, blindness, or epilepsy;

(a3) Spinal cord stimulation for the treatment of pain, paraplegia, spasticity, Parkinson's disease;

(a4) Spinal root stimulation for the treatment of pain, incontinence (a5) Sensory nerve stimulations such as the cochlear stimulation for deafness or optic nerve stimulation for blindness;

(a6) Motor nerve stimulation for the treatment of paralyses of central origin such as drop foot syndrome, phrenic nerve stimulation in respiratory diseases, hypoglossal nerve stimulation in sleep apnoea syndromes;

(a7) Sensory nerve stimulation for the treatment of pain or providing haptic feedback or other sensory modality information in patients with a prosthesis;

(a8) Vagus nerve stimulation for the treatment of epilepsy, depression, pain, inflammatory syndromes, obesity, heart failures;

Similarly it can advantageously be used to stimulate (b) muscular tissues ($Z_{bio}$) in any of the following applications:

(b1) Muscular stimulation for the treatment of scoliosis, various palsies of peripheral origin, respiratory insufficiencies, sleep apnoea syndromes; or (b2) Heart stimulation for the treatment of cardiac arrhythmias.

Extracorporeal optoelectronic stimulating devices according to the present invention can be used for diagnosing nerve and muscle diseases by measuring response latencies, conduction velocities, response amplitudes, stimulation thresholds, or recruitment curves for direct and reflex responses. Such diagnostic methods may include any of the following applications:

(i) Motor nerve test whereby the stimulator activates motor or mixed nerves through the skin while the corresponding mechanical or electrical muscle activity is being recorded.

(ii) Sensory nerve test whereby the stimulator activates sensory nerves through the skin while the resulting nerve compound action potential is being recorded.

(iii) Transcutaneous stimulation of sensory or mixed nerves while recording the evoked potentials at various points along the central path up to the brain.

(iv) Direct transcutaneous muscle stimulation while the corresponding mechanical or electrical muscle activity is being recorded.

Alternatively, an extracorporeal optoelectronic stimulating device of the present invention can be used for therapeutic applications, including transcutaneous stimulation of motor nerves or muscles:

(i) In a prosthetic treatment for paralysis or paresis of central origin, for example the treatment of a 'drop foot syndrome'.

(ii) To maintain the state of the peripheral organs while paralysed central neural structures regenerate and in order to avoid spasticity, bedsores and other complications of the immobilisation.

(iii) To improve the muscle strength in case of local weakness or asymmetry such as in scoliosis.

(iv) In body building and sport training applications.

An extracorporeal optoelectronic stimulating device of the present invention can also be used for therapeutic treatments by transcutaneous stimulation of sensory nerves or sensitive regions:

(i) To reduce pain.

(ii) To present a blind person with a patterned skin stimulation in a sensory substitution device.

(iii) To provide a warning or afferent signal in devices to fight sleepiness.

| REF | DESCRIPTION |
|---|---|
| 1 | photovoltaic cell electrical stimulating circuit |
| 1C | control photovoltaic cell feeding the control source of light (13) |
| 1F | filtering element specific to source of light emission (2) for the stimulating circuit |
| 1R | recovery photovoltaic cell feeding the electrical recovering circuit |
| 1RF | filtering element specific to source of light emission (2R) for the recovering circuit |
| 2 | source of light emission energizing the photovoltaic cell (1) |
| 2R | recovering source of light emission energizing the recovery photovoltaic cell (1R) |
| 3n | positive electrode |
| 3p | negative electrode |
| 4 | source of electrical impulses |
| 5 | electrical capacitance |
| 6 | electrical resistance |
| 7 | light transmission medium, e.g., fibre optic. |
| 7R | light transmission medium, e.g., fibre optic for energizing the recovering circuit |
| 7s | skin |
| 8 | electrical connectors |
| 9 | light emission sensor |
| 10 | photovoltaic diode circuit in photovoltaic cell |
| 11 | diode in photovoltaic diode circuit (10) |
| 12 | source of current (photovoltaic component) in photovoltaic cell |
| 13 | source of control light emission |
| 20 | housing containing at least the source of power (battery) |
| 30 | casing (located adjacent to the tissue to be electrically stimulated) |

The invention claimed is:

1. An optoelectronic stimulating device configured to be used in a medical treatment involving delivering an electrical current to an electrically excitable tissue ($Z_{bio}$) by two electrodes) electrically coupled to said tissue, said optoelectronic stimulating device comprising:
(a) a housing containing a source of electrical impulses, which is electrically connected to
(b) a source of light emission is configured for emitting a radiation and is in optical communication with
(c) a photovoltaic cell electrically connected to two electrodes for establishing two electrical contacts with said tissue and thus forming an electrical stimulating circuit fed by the photovoltaic cell which is configured to be energized by the radiation emitted by the source of light emission, wherein said housing is physically spaced away from the electrodes;
(d) a source of control light emission emitting a light when electrically activated, and
(e) a light emission sensor in optical communication with the source of control light emission and coupled to a processor programmed to record pulses emitted by the source of control light emission, said processor being part of the source of electrical impulses,
and wherein the source of control light emission is located in one of the electrical stimulating circuit, in series with the electrodes and the photovoltaic cell, or a control circuit separate from the electrical stimulating circuit, in series with a control photovoltaic cell which is in optical communication with the same source of light emission as the photovoltaic cell of the stimulating circuit.

2. The optoelectronic stimulating device according to claim 1, wherein the source of electrical impulses (4) is configured to cause the source of light emission to emit calibrated pulses of light of a duration comprised between 1 µs and 10 ms.

3. The optoelectronic stimulating device according to claim 1, wherein the photovoltaic cell is configured, when energized by the source of light emission, to deliver charges comprised between 0.01 and 50 µC.

4. The optoelectronic stimulating device according to claim 1, comprising one of the following configurations:
(a) The housing also contains the source of light emission, the photovoltaic cell and comprises electrical connectors for electrically connecting the photovoltaic cell to the two electrodes to form the electrical stimulating circuit; or
(b) The housing also contains the source of light emission and is connected to a fibre optic for transmitting the light emitted by the source of light emission to the photovoltaic cell enclosed in an encapsulation located spaced away from the housing and, adjacent to the electrodes; or
(c) The encapsulation encloses the photovoltaic cell and the source of light emission which is in electrical contact with the source of electrical impulses contained in the housing.

5. The optoelectronic stimulating device according to claim 1, further comprising,
a recovering source of light emission in optical communication with
a recovery photovoltaic cell electrically connected to the two electrodes for establishing two electrical contacts with said tissue and thus forming an electrical charge recovering circuit in parallel with the electrical stimulating circuit and fed by the recuperating photovoltaic cell,
such that when the recuperating photovoltaic cell is energized by the recuperating source of light emission, a current flows through the tissue in a direction opposite to the current (I1) flowing in the electrical stimulating circuit, so as to remove any electrochemical charge induced at the electrode-tissue interface.

6. The optoelectronic stimulating device according to claim 1, further comprising a DC-blocking circuit comprising a safety capacitance placed in series with the source of light emission.

7. The optoelectronic stimulating device according to claim 1, wherein the photovoltaic cell comprises a single photovoltaic diode circuit.

8. The optoelectronic stimulating device according to claim 1, in the form of an implant, designed such that at least the electrodes can be implanted at the tissue to be electrically stimulated, a housing containing at least the source of electrical impulses can be implanted at a location remote from the tissue to be electrically stimulated.

9. The optoelectronic stimulating device according to claim 8, further comprising a casing containing at least the photovoltaic cell can be implanted adjacent to the electrodes and to the tissue to be electrically stimulated.

10. The optoelectronic stimulating device according to claim 1, wherein the electrically excitable tissue ($Z_{bio}$) to be fed with electrical current is selected from (a) neural tissues and (b) muscular tissues.

11. The optoelectronic stimulating device according to claim 1, configured to be used in one or more of the following stimulations:
(a1) Deep brain stimulation for the treatment of Parkinson's disease, epilepsy, depression, obsessive compulsive disorder, dystonia, essential tremor, pain, or blindness;
(a2) Cortical brain stimulation for the treatment of deafness, blindness, or epilepsy;
(a3) Spinal cord stimulation for the treatment of pain, paraplegia, spasticity, Parkinson's disease;
(a4) Spinal root stimulation for the treatment of pain, incontinence
(a5) Sensory nerve stimulations such as the cochlear stimulation for deafness or optic nerve stimulation for blindness;
(a6) Motor nerve stimulation for the treatment of paralyses of central origin such as drop foot syndrome, phrenic nerve stimulation in respiratory diseases, hypoglossal nerve stimulation in sleep apnoea syndromes;
(a7) Sensory nerve stimulation for the treatment of pain or providing haptic feedback or other sensory modality information in patients with a prosthesis;
(a8) Vagus nerve stimulation for the treatment of epilepsy, depression, pain, inflammatory syndromes, obesity, heart failures;
(b1) Muscular stimulation for the treatment of scoliosis, various palsies of peripheral origin, respiratory insufficiencies, sleep apnoea syndromes; or
(b2) Heart stimulation for the treatment of cardiac arythmias.

12. The optoelectronic stimulating device according to claim 1, configured to be used in one or more of the following stimulations:
(a) Diagnostic of nerve and muscle diseases by measuring response latencies, conduction velocities, response amplitudes, stimulation thresholds, recruitment curves for direct and reflex responses in the following structures:
(i) Motor nerve test whereby the stimulator activates motor or mixed nerves through the skin while the corresponding mechanical or electrical muscle activity is being recorded,
(ii) Sensory nerve test whereby the stimulator activates sensory nerves through the skin while the resulting nerve compound action potential is being recorded,
(iii) Transcutaneous stimulation of sensory or mixed nerves while recording the evoked potentials at various points along the central path up to the brain, or (iv) Direct transcutaneous muscle stimulation while the corresponding mechanical or electrical muscle activity is being recorded,
(b) Therapeutic treatment by transcutaneous stimulation of motor nerves or muscles:
  (i) In a prosthetic treatment for paralysis or paresis of central origin, for example the treatment of a 'drop foot syndrome',
  (ii) To maintain the state of the peripheral organs while paralysed central neural structures regenerate and in order to avoid spasticity, bedsores and other complications of the immobilisation,
  (iii) To improve the muscle strength in case of local weakness or asymmetry such as in scoliosis, or
  (iv) In body building and sport training applications,
(c) Therapeutic treatment by transcutaneous stimulation of sensory nerves or sensitive regions
  (i) To reduce pain,
  (ii) To present a blind person with a patterned skin stimulation in a sensory substitution device,
  (iii) To provide a warning or afferent signal in devices to fight sleepiness.

13. The optoelectronic stimulating device according to claim 1, wherein the housing also contains the source of light emission and is connected to a fibre optic for transmitting the light emitted by the source of light emission to the photovoltaic cell enclosed in a casing located separate from the hoising and adjacent to the electrodes.

14. The optoelectronic stimulating device according to claim 1, wherein an encapsulation encloses the photovoltaic cell and the source of light emission which is in electrical contact with the source of electrical impulses contained in the housing.

15. The optoelectronic stimulating device according to claim 1, wherein the photovoltaic cell comprises N photovoltaic diode circuits arranged in series to control the voltage of the photovoltaic cell, wherein $N \geq 2$.

16. The optoelectronic stimulating device according to claim 1, wherein the photovoltaic cell is configured, when energized by the source of light emission, to deliver charges comprised between 0.1 and 10 μC.

* * * * *